United States Patent [19]

van Andel

[11] Patent Number: Plant 5,526

[45] Date of Patent: Jul. 30, 1985

[54] CARNATION NAMED STANOKER

[75] Inventor: Jacob van Andel, Aalsmeer, Netherlands

[73] Assignees: B. V. Handelskwekerij; M. C. van Staaveren, both of Aalsmeer, Netherlands

[21] Appl. No.: 556,683

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill
*Attorney, Agent, or Firm*—Chas. W. Rummler

[57] ABSTRACT

A new variety of carnation plant of a solid deep yellow coloration characterized by a vigorous growth and continuous blooming habit, and the stability of the flower color which is the same for all seasons.

1 Drawing Figure

BACKGROUND OF THE NEW PLANT

This new carnation plant was discovered by me at Aalsmeer, Holland, in 1977 as a sport of the carnation variety "Londorga" (unpatented) growing in greenhouse among a stand of plants of the parent variety being grown for commercial purposes. Because of the new flower color and size of the discovery bloom, I decided to propagate it for test and observation and that was done by means of cuttings from the discovery plant at Aalsmeer, Holland, with such success that this kind of propagation was carried on through several successive generations, which demonstrated conclusively that the novel characteristics of both growth habit and flower color would hold true from generation to generation and appeared to be firmly fixed.

DESCRIPTION OF THE DRAWING

My new variety of carnation plant is illustrated by the accompanying photographic drawing which shows, a three-quarter view and a partial face view of fully opened blooms, one of which has been hand painted to show the true color of the blooms.

DESCRIPTION OF THE NEW PLANT

The following is a detailed description of my new carnation plant based upon observation of greenhouse grown plants made at Aalsmeer, Holland, in the summer of 1983, the color designations being according to The R.H.S. Colour Chart of The Royal Horticultural Society at London, England.

THE PLANT

Origin: Sport.
Parentage: The carnation variety "Londorga" (unpatented).
Classification:
*Botanic.*—Hybrid *Dianthus caryophyllus.*
*Commercial.*—Greenhouse carnation for cut flowers.
Form: Leafy bush.
Height: Average.
Growth: Vigorous and upright with normal branching.
Foliage: Abundant with quantity depending upon season.
*Size of leaf.*—Medium.
*Shape.*—Oblong.

*Color.*—Upper side and under side — Blue/Green with waxy layer.
*Texture.*—Smooth.

THE BUD

Size: Medium.
Form: Cylindrical.
*Diameter.*—About 1.5 cm.
*Length.*—About 3 cm.
Opening rate: Normal.
Color of petals:
*When sepals divide and petals begin to unfurl-*.—R.H.S. 11A/B.
Sepals: Average size and generally curl back when flowers open.
*Number.*—Five.
*Color.*—Inside and outside — Grey/Green.
Calyx:
*Size.*—Medium.
*Splitting.*—Hardly ever.
*Aspect.*—Smooth.

THE FLOWER

Blooming habit: Continuous.
Size of bloom: Medium.
*Diameter.*—About 8 cm.
*Depth.*—About 4 cm.
Borne: Singly.
Shape: High centered.
Petalage:
*Number of petals.*—50 To 60.
*Arrangement.*—Imbricated.
*Form.*—Fan-shaped with serrated margins.
*Texture.*—Soft.
*Appearance.*—Shiny.
*color.*—All petals in all seasons: Upper side —R.H.S. 11A/B. Under side —R.H.S. 11A/B.
Peduncle:
*Length.*—Depends upon season.
*Color.*—Dark Green.
*Character.*—Strong and upright.
Persistence: Flower petals hang on and dry.
Fragrance: The bloom is slightly fragrant.
Disease resistance: This bloom is less susceptible to *Fusarium oxysporum* as observed at Aalsmeer, Holland.
Lasting quality:
*On plant.*—20 days.

*As cut flower.*—10 To 15 days.

REPRODUCTIVE ORGANS

Stamens:

*Number.*—Average.

*Anthers.*—Size: Medium. Color: Cream.

*Pollen.*—Color: Cream (if present).

Pistils:

*Number.*—One.

*Style.*—Length: Approximately 30 mm.

This new variety most nearly resembles the variety "Harvest Moon". The flower color, however, is quite new and compared to "Harvest Moon", the plant is less susceptible to *Fusarium oxysporum.*

I claim:

1. The new and distinct variety of carnation plant, substantially as herein shown and described, characterized by its continuous year round production of deep yellow blooms of relatively large size, and by the stability of the flower color which holds throughout all seasons.

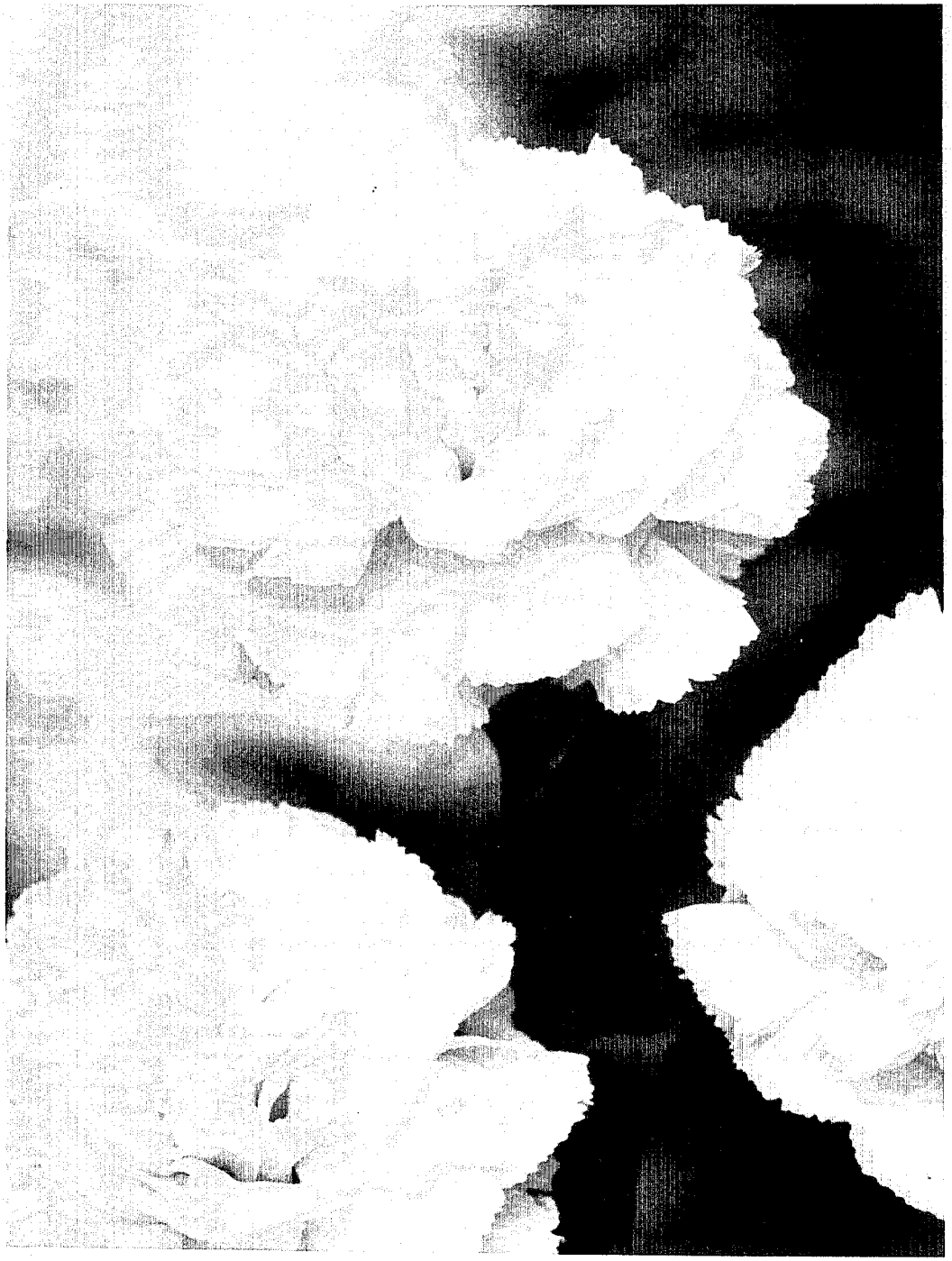

* * * * *